(12) United States Patent
Kilambi et al.

(10) Patent No.: US 8,282,738 B2
(45) Date of Patent: Oct. 9, 2012

(54) SOLVO-THERMAL FRACTIONATION OF BIOMASS

(75) Inventors: Srinivas Kilambi, Marietta, GA (US); Kiran L. Kadam, Marietta, GA (US)

(73) Assignee: Renmatix, Inc., Kennesaw, GA (US)

( * ) Notice: Subject to any disclaimer, the term of this patent is extended or adjusted under 35 U.S.C. 154(b) by 337 days.

(21) Appl. No.: 12/504,636

(22) Filed: Jul. 16, 2009

(65) Prior Publication Data
US 2010/0043782 A1 Feb. 25, 2010

Related U.S. Application Data

(60) Provisional application No. 61/081,337, filed on Jul. 16, 2008, provisional application No. 61/081,348, filed on Jul. 16, 2008, provisional application No. 61/092,680, filed on Aug. 28, 2008, provisional application No. 61/224,809, filed on Jul. 10, 2009.

(51) Int. Cl.
*C13K 13/00* (2006.01)
(52) U.S. Cl. ............................................. 127/1
(58) Field of Classification Search ........................ None
See application file for complete search history.

(56) References Cited

U.S. PATENT DOCUMENTS

| | | |
|---|---|---|
| 4,308,200 A | 12/1981 | Fremont |
| 4,338,199 A | 7/1982 | Modell |
| 4,366,322 A | 12/1982 | Raymond |
| 4,493,797 A | 1/1985 | Avedesian |
| 4,543,190 A | 9/1985 | Modell |
| 4,675,198 A | 6/1987 | Sevenants |
| 5,009,746 A | 4/1991 | Hossain et al. |
| 5,328,934 A | 7/1994 | Schiraldi |
| 5,512,231 A | 4/1996 | Thies et al. |
| 5,516,952 A | 5/1996 | Lee et al. |
| 5,536,325 A | 7/1996 | Brink |
| 5,628,830 A | 5/1997 | Brink |
| 5,788,812 A | 8/1998 | Agar et al. |
| 5,830,763 A | 11/1998 | Junk et al. |
| 6,180,845 B1 | 1/2001 | Catallo et al. |

(Continued)

FOREIGN PATENT DOCUMENTS

CN 102239184 11/2011
(Continued)

OTHER PUBLICATIONS

Pasqunini et al, extraction of lignin from sugar cane bagasse and pinus taeda wood chips using ethanol-water mixtures and crabon dioxide at high pressures, 2005, j. of supercritical fluids, pp. 31-39.*

(Continued)

*Primary Examiner* — Melvin C Mayes
*Assistant Examiner* — Stefanie Cohen
(74) *Attorney, Agent, or Firm* — Kilpatrick Townsend & Stockton LLP

(57) ABSTRACT

The invention relates to a process for producing xylose and cellulose from a biomass comprising: (a) mixing a biomass with a reactive fluid comprising water and a supercritical $C_1$-$C_5$ alcohol to form a mixture at a first temperature and a first pressure; (b) maintaining the mixture at the first temperature and first pressure for a first time period, wherein a reaction occurs; and (c) quenching the reaction to form at least one reaction product mixture; wherein xylose and cellulose are produced by the process. Lignin may also be produced by the processes of the invention.

17 Claims, 5 Drawing Sheets

U.S. PATENT DOCUMENTS

| | | | |
|---|---|---|---|
| 6,555,350 | B2 | 4/2003 | Ahring et al. |
| 6,642,396 | B1 | 11/2003 | Zeitsch et al. |
| 6,743,928 | B1 | 6/2004 | Zeitsch |
| 6,921,820 | B2 | 7/2005 | Arai et al. |
| 7,189,306 | B2 | 3/2007 | Gervais |
| 7,476,296 | B2 | 1/2009 | Appel et al. |
| 7,566,383 | B2 | 7/2009 | Everett et al. |
| 7,666,637 | B2 | 2/2010 | Nguyen |
| 7,771,699 | B2 | 8/2010 | Adams et al. |
| 8,057,639 | B2 | 11/2011 | Pschorn et al. |
| 8,119,823 | B2 | 2/2012 | Kilambi |
| 2007/0161095 | A1 | 7/2007 | Gurin |
| 2007/0267008 | A1 | 11/2007 | Funazukuri et al. |
| 2008/0015336 | A1 | 1/2008 | Cornish et al. |
| 2008/0295981 | A1 | 12/2008 | Shin et al. |
| 2008/0302492 | A1 | 12/2008 | Shin et al. |
| 2009/0056201 | A1 | 3/2009 | Morgan |
| 2009/0288788 | A1 | 11/2009 | Castor |
| 2010/0004119 | A1 | 1/2010 | Gadkaree |
| 2010/0012583 | A1 | 1/2010 | Stuart |
| 2010/0048884 | A1 | 2/2010 | Kilambi |
| 2010/0048924 | A1 | 2/2010 | Kilambi |
| 2010/0069626 | A1 | 3/2010 | Kilambi |
| 2011/0079219 | A1 | 4/2011 | Mcdonald et al. |

FOREIGN PATENT DOCUMENTS

| | | | |
|---|---|---|---|
| DE | 10259928 | A1 | 7/2004 |
| JP | 2005296906 | A * | 10/2005 |
| WO | 0160752 | | 8/2001 |
| WO | 0204524 | | 1/2002 |
| WO | 02070753 | | 9/2002 |
| WO | WO-2007056701 | | 5/2007 |
| WO | 2008026932 | | 3/2008 |
| WO | 2008036500 | | 3/2008 |
| WO | WO-2009015409 | | 2/2009 |
| WO | 2009108773 | | 9/2009 |
| WO | WO-2010009343 | | 1/2010 |
| WO | 2010113129 | | 10/2010 |
| WO | 2010121367 | | 10/2010 |
| WO | 2011002822 | | 1/2011 |
| WO | 2011091044 | | 7/2011 |
| WO | WO-2011091044 | | 7/2011 |

OTHER PUBLICATIONS

Pasquini, Daniel et al., "Sugar cane bagasse pulping using supercritical $CO^2$ associated with co-solvent 1-butanol/water", J. of Supercritical Fluids, vol. 34; pp. 125-134 (2005).

Schacht, Christian et al., "From plant materials to ethanol by means of supercritical fluid technology", J. of Supercritical Fluids, vol. 46; pp. 299-321 (2008).

PCT Application No. PCT/US2009/050898, International Preliminary Report on Patentability mailed Jan. 18, 2011.

PCT Application No. PCT/US2009/050898, International Search Report and Written Opinion mailed Feb. 8, 2010.

"Supercritical Fluids", Kirk-Othmer Encyclopedia of Chemical Technology 3rd ed., John Wiley & Sons, New York.

Adschiri, et al., "Noncatalytic Conversion of Cellulose in Supercritical and Sub-Critical Water", Journal of Chemical Engineering of Japan, 1993, 26(6):676-680.

Bennett, et al., "Chemicals from Forest Products by Supercritical Fluid Extraction", Fluid Phase Equil., 1983, 10:337.

Bicker, et al., "Catalytical conversion of carbohydrates in subcritical water: A new chemical process for lactic acid production", Journal of Molecular Catalysis A: Chemical 239, 2005, 151-157.

Boocock, et al., "Liquefaction of Biomass by Rapid Hydrolysis", Can. J. Chem. Eng., 1983, 61:80.

Chamblee, et al., "Reversible in situ acid formation for β—pinene hydrolysis using $CO_2$ expanded liquid and hot water", Green Chemistry, 2004, vol. 6, 382-386.

Dias, et al. "Dehydration of xylose into fufural over micro-mesoporous sulfonic acid catalysts", Journal of Catalysis 229, 2005, 414-423.

Eckert, et al., "Environmental Science and Technology", 1986, 20:319-325.

Ehara, et al. "A comparative study on chemical conversion of cellulose between the batch-type and flow-type in supercritical water", Cellulose, 2002, 9:301-311.

Ehara, et al. "Chemical conversion of woody biomass by supercritical water -Degradation of lignin-", Graduate School of Energy Science, Kyoto University, Kyoto Japan.

Erzengin, et al., "Liquefaction of Sunflower Stalk by Using Supercritical Extraction", Energy Conversion and Management, Elsevier Science Publishers, Oxford, GB Aug. 1998, 39:11, 1203-1206.

Guirong, et al., "Cellulose decomposition behavior in hot-compressed aprotic solvents", Science in China Series B: Chemistry, May 2008, vol. 51, No. 5, 479-486.

Houghton, et al., "Reactivity of Some Organic Compounds with Supercritical Water", Fuel 1986, 61:827.

Kim, et al., "Selective Synthesis of Furfural from Xylose with Supercritical Carbon Dioxide and Solid Acid Catalyst", Journal of Industrial and Engineering Chemistry, The Korean Society of Industrial and Engineering Chemistry, Korea 2001, 7(6); 424-429.

Knopf, et al., "Reactive Extraction of Lignin from Biomass Using Supercritical Ammonia-Water Mixtures", J. Supercritical Fluids 1993, 6:249-254.

Li, et al., "Interaction of Supercritical Fluids with Lignocellulosic Materials", Industrial and Engineering Chemistry Research 1988, 27(7): 1301-1312.

Marchessault, et al., "A New Understanding of the Carbohydrate System", Future Sources of Organic Raw Materials 1980, 613-625.

Matsumura, et al. "Supercritical Water Treatment of Biomass for Energy and Material Recovery", Combust. Sci. and Tech., 2006, 178: 509-536.

McCoy, et al., "Extraction of Lignin from Biomass with Supercritical Alcohol", J. Supercritical Fluids 1989, 2:80-84.

McHugh, et al., "Supercritical Fluid Extraction : Principles and Practice", Butterworths 1986, 309-310.

Miyazawa, et al., "Polysaccharide Hydrolysis Accelerated by Adding Carbon Dioxide under Hydrothermal Conditions", Biotechnol. Prog. 2005, 21:1782-1785.

Modell, et al., "Supercritical Water Oxidation of Pulp Mill Sludges", Tappi J. 1992, 75:195.

Ogihara, et al. "Direct observation of cellulose dissolution in subcritical and supercritical water over a wide range of water densities (500-1000 $kg/m^3$ )", Cellulose, 2005, 12:595-606.

Osada, et al., "Low Temperature Catalytic Gasification of Lignin and Cellulose with a Ruthenium Catalyst in Supercritical Water", Energy Fuels 2004 , 18: 327-333.

Pasquini, et al., "Extraction of Lignin from sugar cane bagasse and *Pinus taeda* wood chips using ethanol-water mixtures and carbon dioxide at high pressures", Journal of Supercritical Fluids, PRA Press, US Nov. 2005, 36(1); 31-39.

Persson, et al., "Supercritical Fluid Extraction of a Lignocellulosic Hydrolysate of Spruce for Detoxification and to Facilitate Analysis of Inhibitors", Biotechnology and Bioengineering, Wiley & Sons , Hoboken, NJ, US Sep. 20, 2002, 79(6):694-700.

Peter, et al., "High Pressure Extraction of Lignin from Biomass", Supercritical Fluid Technology, p. 385 (1985).

Rao, et al., "Pyrolysis Rates of Biomass Materials", Energy 1998, 23:973-978.

Sako, "Kinetic study of furfural formation accompanying supercritical carbon dioxide extraction", Journal of Chemical Engineering of Japan, Society of Chemical Engineers Aug. 1, 1992, 25(4):372-377.

Sangarunlert, et al., "Furfural production by acid hydrolysis and supercritical carbon dioxide extraction from rice husk", Korean Journal of Chemical Engineering 2007, 24(6): 936-941.

Sasaki, et al., "Cellulose Hydrolysis in Sub-Critical and Supercritical Water", Journal of Supercritical Fluids 1998, 13:261-268.

Sina, et al. "Key Compounds of the Hydropyrolysis of Glucose in Supercritical Water in the Presence of $K_2CO_3$", Ind. Eng. Chem. Res., 2003, 42(15), 3516-3521.

Walsum, et al. "Carbonic acid enhancement of hydrolysis in aqueous pretreatment of corn stover", Bioresource Technology 93, 2004, 271-226.

Yoshida, et al., "Gasification of Biomass Model Compound and Real Biomass in Supercritical Water", Biomass and Bioenergy, 26:71-78 (2004).

International PCT Application No. PCT/US2011/21726, International Search Report and Written Opinion dated Jul. 5, 2011.

Holgate, et al., "Glucose Hydrolysis and Oxidation in Supercritical Water", AlChE Journal, 1995, 41(3), 637-636.

Li, et al., "Interaction of Supercritical Fluids with Lignocellulosic Materials", Industrial Engineering Chemistry Research, American Chemical Society Res., Jul. 1988, 27(7):1301-1312.

Lu, et al., "Decomposition of Cellulose to Produce 5-hydroxymethylfuraldehyde in Subcritical Water", Abstract of Transactions of Tranjin University, STN Accession No. 2008:1016799, Document No. 151:427986, 2008, 14(3), 198-201.

Moreschi, et al., "Hydrolysis of Ginger Bagasse Starch in Subcritical Water and Carbon Dioxide", Journal of Agricultural and Food Chemistry, 2004, 52(6), 1753-1758.

Saito, et al., "The Investigation of Degradation Reaction of Various Saccharides in High Temperature and High Pressure Water", Journal of Physics:Conference Series, 2008, 121.

Wiboonsiriku, et al., "Properties of Extracts from Defatted Rice Bran by its Subcritical Water Treatment", Journal of Agricultural and Food Chemistry, 2007, 55(21), 8759-8765.

Zhao, et al., "Supercritical hydrolysis of cellulose for oligosaccharide production in combined technology", Chemical Engineering Journal, Aug. 1, 2009, 150(2):411-417.

U.S. Appl. No. 12/504,611, Office Action mailed Sep. 23, 2011.

U.S. Appl. No. 12/504,613, Non-Final Office Action mailed Sep. 26, 2011.

U.S. Appl. No. 12/504,628, Non-Final Office Action mailed Aug. 8, 2011.

U.S. Appl. No. 12/504,628, Response to Office Action filed Oct. 27, 2011.

U.S. Appl. No. 12/504,628, Supplemental Response filed Nov. 14, 2011.

U.S. Appl. No. 12/504,628, Notice of Allowance mailed Dec. 7, 2011.

Pasquini, Daniel et al., "Sugar cane bagasse pulping using supercritical CO2 associated with co-solvent 1-butanol/water", J. of Supercritical Fluids, 2005, 34; 125-134.

Schacht, Christian et al., "From plant materials to ethanol by means of supercritical fluid technology", J. of Supercritical Fluids, 2008, 46; 299-321.

"Merriam-Webster Dictionary, Quench-Definition", document available at: http://www.merriam-webster.com/dictionary/quench, Retrieved on Feb. 9, 2012 (1 pages).

U.S. Appl. No. 12/504,611, "Response to Non-Final Office Action" mailed Dec. 22, 2011 (11 pages).

U.S. Appl. No. 12/504,611, "Final Office Action" mailed Jan. 30, 2012 (17 pages).

U.S. Appl. No. 12/504,611, "Response to Final Office Action" mailed May 30, 2012 (22 pages).

U.S. Appl. No. 12/504,613, "Response to Non-Final Office Action", mailed Dec. 22, 2011 (11 pages).

U.S. Appl. No. 12/504,613, "Final Office Action", mailed Feb. 2, 2012 (23 pages).

U.S. Appl. No. 12/504,613, "Response to Final Office Action", mailed May 30, 2012 (11 pages).

European Patent Application No. 09790548.3, "Article 94(3) EPC" mailed Mar. 30, 2012 (8 pages).

* cited by examiner

SOLVO-THERMAL FRACTIONATION OF BIOMASS

CROSS-REFERENCE TO RELATED APPLICATIONS

This application claims priority to U.S. Provisional Patent Application No. 61/081,337 filed Jul. 16, 2008, U.S. Provisional Patent Application No. 61/081,348 filed Jul. 16, 2008, U.S. Provisional Patent Application No. 61/092,680 filed Aug. 28, 2008, and U.S. Provisional Patent Application No. 61/224,809 filed Jul. 10, 2009, the disclosures of each of which are incorporated herein by reference in their entireties. This application is related to and incorporates by reference the following PCT application filed on even date herewith: "NANO-CATALYTIC-SOLVO-THERMAL TECHNOLOGY PLATFORM BIO-REFINERIES", inventors Srinivas Kilambi and Kiran L. Kadam.

STATEMENT OF RIGHTS TO INVENTIONS MADE UNDER FEDERALLY SPONSORED RESEARCH

Not applicable

BACKGROUND OF THE INVENTION

Supercritical solvents such as supercritical water (SCW) and supercritical carbon dioxide ($SCCO_2$) have been used in extracting various substances and assisting chemical reactions. For example, U.S. Pat. No. 5,516,952 presents a process for breaking down natural, synthetic, vulcanized, and non-vulcanized rubbers. U.S. Pat. No. 5,830,763 describes a process for the preparation of organic and inorganic deuterium-tagged compounds by heating with deuterium oxide under supercritical conditions. U.S. Pat. No. 6,180,845 describes a process for the fractionation of waste biomass into a hydrocarbon mixture. U.S. Pat. Nos. 4,543,190 and 4,338,199 describe processes for the oxidation of organic compounds in supercritical water.

D. Boocock et al., "Liquefaction of biomass by rapid hydrolysis" *Can. J. Chem. Eng.*, 61:80 (1983) discloses the use of supercritical water to liquefy biomass. Peter et al., "High pressure extraction of lignin from biomass" *Supercritical fluid technology, p.* 385 (1985) discloses the use of supercritical fluids to extract lignin from biomass. Houghton et al., "Reactivity of some organic compounds with supercritical water" *Fuel*, 61:827 (1986) discloses the use of supercritical fluids to decompose some organic compounds. Modell et al., "Supercritical water oxidation of pulp mill sludges" *TAPPI J.*, 75:195 (1992) discusses the use of supercritical water for the oxidation of pulp mill sludges. B. Potic et al., "Gasification of Biomass model compound and real biomass in Supercritical Water," *Biomass and Bioenergy*, 26:71-78 (2004); F. C. Knopf et al., "Reactive Extraction of Lignin from biomass using supercritical ammonia-water mixtures" *J. Supercritical Fluids*, 6:249-254 (1993); B. J. McCoy et al., "Extraction of Lignin from biomass with supercritical alcohol" *J. Supercritical Fluids*, 2:80-84 (1989); and B. Bennett et al., "Chemicals from forest products by supercritical fluid extraction" *Fluid Phase Equil.*, 10:337 (1983) also provide further background information on use of supercritical fluids.

Methods for efficiently converting biomass from renewable resources or waste materials to more valuable products are desirable.

BRIEF SUMMARY OF THE INVENTION

Disclosed are various methods, apparatus configurations, and compositions involved in converting biomass to more valuable products.

In one instance, a method involves processing a water-containing biomass with supercritical alcohol and supercritical carbon dioxide to fractionate the biomass and obtain carbonaceous and other products that may be sold or further processed. In another instance, a method involves processing a biomass with supercritical alcohol, supercritical carbon dioxide, and additional sub-critical or near-critical water to fractionate and obtain products as described above. In yet another instance, a method includes two stages: the first stage involves processing a biomass with supercritical carbon dioxide and sub-critical water to hydrolyze hemicellulose thus separating the hemicellulose from the remaining solids; the second stage involves further processing the remaining solids from the first stage using an alcohol under supercritical or sub-critical conditions to extract lignin thus separating the lignin from the cellulose solids. In each instance, conditions are maintained so that the temperature and pressure are below the critical point for water. Products of fractionation may include one or more of cellulose, lignin, and xylose.

In another instance, provided is a two stage process for fractionating a biomass comprising: (a) forming a first reactant mixture comprising a biomass, water and $CO_2$ at a first temperature and a first pressure; (b) maintaining the first reactant mixture at the first temperature and the first pressure for a first time period, wherein the $CO_2$ is supercritical and the water is sub-critical, and wherein a first reaction occurs; (c) recovering a solid from the first reaction mixture; (d) contacting the solid with a second fluid comprising a $C_1$-$C_5$ alcohol to form a second reactant mixture at a second temperature and a second pressure; (e) maintaining the second reactant mixture at the second temperature and the second pressure for a second time period, wherein a second reaction occurs; and (f) quenching the second reaction to form at least one reaction product mixture.

Also provided is a system for fractionating biomass comprising: a reactor configured for contacting a biomass with a reactive fluid at a temperature and pressure above the critical point of carbon dioxide but at least one of the temperature and pressure of the fluid is beneath the critical temperature and pressure for water; a heating device configured for heating the reactive fluid to the desired temperature; a back-pressure regulator located downstream of the reactor for maintaining the desired pressure; and a heat exchanger configured for cooling the reaction and located downstream of the reactor. In some embodiments, the system may further comprise a filtration device configured for separating at least a portion of the fractionated product in solid state from the fractioned and cooled reaction mixture.

Also disclosed is a method of making amorphous cellulose in which, subsequent to a method as discussed above, the reaction product mixture is expanded sufficiently rapidly to destroy crystalline structure of the cellulose, resulting in amorphous cellulose.

Products obtained may include a solution of lignin and optionally xylose/XOS in an aqueous alcoholic phase in conjunction with cellulose in a carbonic acid phase; a slurry of biomass, supercritical, and subcritical fluids as described in the paragraph above; a slurry of biomass, supercritical, and subcritical fluids as described above as well as one or more products of interest such as a glucan (particularly cellulose), xylose, xylose oligosaccharides (XOS), hemicellulose, and/ or lignin; and a solution of e.g. xylose in an aqueous alcohol and/or carbonic acid phase. Amorphous cellulose is also provided.

Also provided is a composition as described herein, including reaction intermediates as described, or a product produced by any of the processes as described herein or a portion of the processes described. Also provided is a system for producing any of the compositions described herein, or for performing any of the methods or a portion of a method as described herein.

Other methods and compositions are apparent from the disclosure herein.

DETAILED DESCRIPTION OF THE INVENTION

Figure 1:
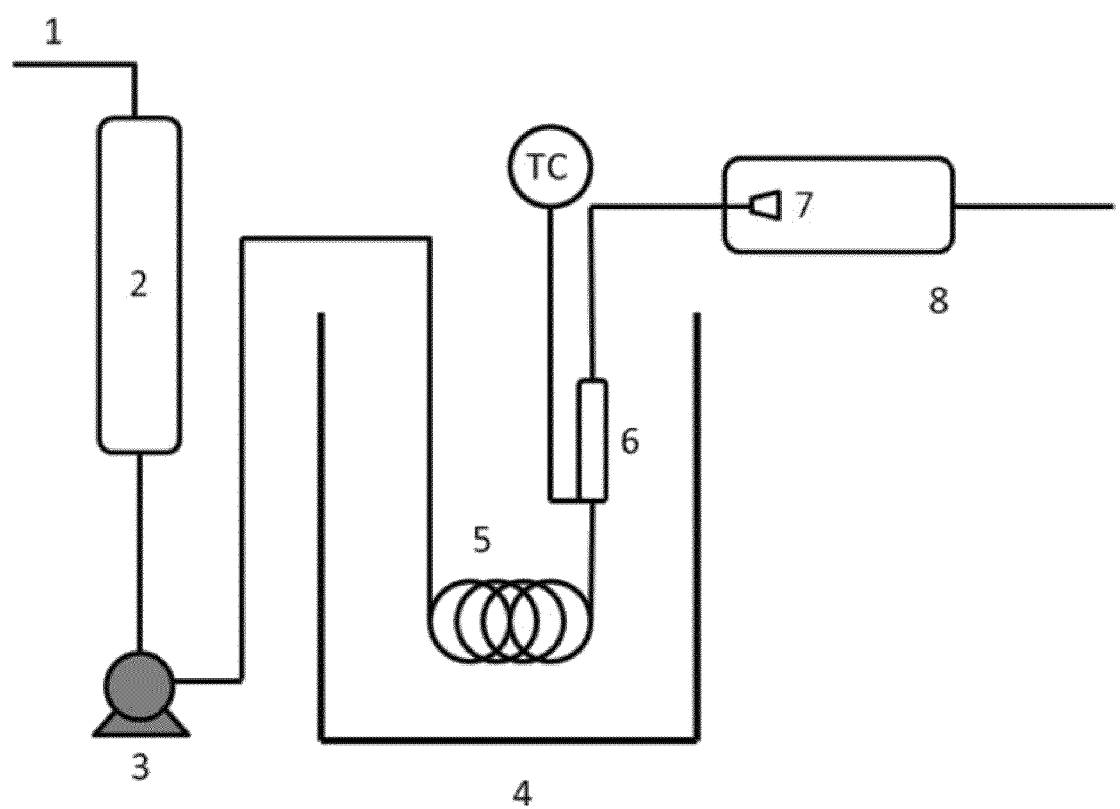
FIG. 1 depicts a schematic of the experimental setup for one embodiment of a semi-batch process. (1) $CO_2$ source (2) Ethanol or Ethanol/Water reservoir (3) HPLC pump (4) Heated sand bath (5) Preheating coil (6) Feedstock packed bed (7) Expansion nozzle (8) Product containment/collection; (TC) thermocouple.

The invention provides a process for fractionating a biomass, using water and a supercritical $C_1$-$C_5$ alcohol. The processes described herein provide methods for producing cellulose, xylose, xylose oligosaccharides (XOS) and/or lignin from biomass.

A supercritical fluid is a fluid at a temperature above its critical temperature and at a pressure above its critical pressure. A supercritical fluid exists at or above its "critical point", the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, the critical temperature is about 374.2° C., and the critical pressure is about 221 bar. Carbon dioxide has a critical point of about 31° C. and about 72.9 atmospheres (about 1072 psig). Ethanol has a critical point of about 243° C. and about 63 atmospheres. Methanol has a critical point of about 923.0° R (512.8° K) and about 1174.0 psia (80.9 bar). The critical point for other alcohols can be ascertained from the literature or experimentally.

Near-critical water has a temperature at or above about 300° C. and below the critical temperature, and near-critical water has a pressure of at least about 225 bar. Sub-critical water has a temperature of less than about 300° C. and a pressure of at least about 225 bar. Sub-critical water temperature may be greater than about 250° C. and less than about 300° C., and in many instances sub-critical water has a temperature between about 250° C. and about 280° C.

As used herein, a fluid which is "supercritical" (e.g. supercritical water, supercritical ethanol, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of subcritical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of subcritical water and supercritical $CO_2$ may have a temperature of about 250° C. to about 280° C. and a pressure of at least about 225 bar.

The term "reactive fluid" used herein means a fluid that is at a temperature higher than the boiling point of the liquid state of the fluid under atmospheric pressure (1 atm). The reactive fluid may be a liquid, a gas, a supercritical fluid, or a mixture of these. For example, water at a temperature above 100° C. and under atmospheric pressure is considered a reactive fluid. Supercritical, near-critical, and sub-critical fluids are reactive fluids, illustrative examples including but not limited to sub-critical water, near critical water, supercritical water, supercritical ethanol, and supercritical $CO_2$.

As used herein, "$C_1$-$C_5$ alcohol" indicates an alcohol comprising 1 to 5 carbon atoms. Examples of $C_1$-$C_5$ alcohols include, but are not limited to, methanol, ethanol, n-propanol, isopropanol, n-butanol, s-butanol, t-butanol, i-butanol, n-pentanol, 2-pentanol, 3-pentanol, 2-methyl-1-butanol, 2-methyl-2-butanol, 3-methyl-1-butanol, 3-methyl-2-butanol, and 2,2-dimethyl-1-propanol. Mixtures of these alcohols may be used.

We have developed a new approach to hydrothermal processing (HTP) called Solvothermal Processing (STP) that uses one or more supercritical $C_1$-$C_5$ alcohols in combination with hot compressed water, and optionally including $CO_2$, for biomass fractionation to produce value-added chemical products. Biomass comprises glucan, hemicellulose, and may additionally comprise lignin. Briefly, biomass is reacted under hydrothermal conditions (using water and supercritical $C_1$-$C_5$ alcohol, and optionally $CO_2$), producing cellulose, xylose and/or xylose oligosaccharides (xylose/XOS) (from hemicellulose), and additionally, when the biomass is a lignocellulosic biomass, lignin. The cellulose is insoluble in the aqueous alcoholic phase, and the xylose and lignin are soluble in the aqueous alcoholic phase. The alcohol (e.g. ethanol) may enhance the recovery of water-insoluble, lignin-derived compounds. Marchessault and St-Pierre observed that hydrothermally treated lignin coalesces into small spheres of less than 5-10 μm diameter that are readily soluble in aqueous organic solvents, such as ethanol-water (Marchessault, R. H., St-Pierre, J. M. "A New Understanding of the Carbohydrate System" In I, Chemrawn, L. E. St-Pierre, and G. R. Brown (Eds.), Future Sources of Organic Raw Materials: 613-625. Pergamon Press, Oxford. 1980). The instant invention avoids lignin precipitation via the addition of alcohol to the water phase, which allows both cleanly fractionated cellulose and high quality lignin to be separately recovered. After evaporation of alcohol from the solvent mixture, the lignin precipitates out of solution, and the xylose (which is water soluble) remains in solution (see e.g. FIG. 2). These products may be separated and used to form other value-added products, as further described in U.S. Provisional Patent Application No. 61/081,341 titled "Solvo-Thermal Hydrolysis of Xylose" and U.S. Provisional Patent Application No. 61/081,346 titled "Solvo-Thermal Hydrolysis of Cellulose", which are herein incorporated by reference in their entirety.

Without wishing to be bound by theory, the addition of carbon dioxide to the reactant mixture promotes the formation of carbonic acid, which enhances the hydrolysis of hemicellulose at relatively low reaction severity, forming xylose and other C5 and C6 sugars. Addition of $CO_2$ allows for the ability to adjust reaction acidity without the addition of strong acids or bases which are more prone to form degradation products via side reactions, and which can lead to disposal problems (such as with gypsum that is formed during neutralization of acidic hydrolyzates). Also, $CO_2$ can be recovered and recycled. Initial studies by Miyazawa and Funazukuri showed that the addition of $CO_2$ significantly enhanced polysaccharide hydrolysis rates (in some cases by 10-fold), increased yields of monomeric sugars, and suppressed the formation of hydroxymethylfuran (HMF) byproducts relative to that observed with comparable mineral acid catalyzed processes (Miyazawa, T. and Funazukuri, T. "Polysaccharide hydrolysis accelerated by adding carbon dioxide under hydrothermal conditions" *Biotechnol. Prog.* 2005, 21:1782-1785). In some embodiments, addition of $CO_2$ to the hot water-supercritical ethanol process increases the concentration of xylose extracted by the process, and may additionally reduce the amount of organic acids produced.

Therefore, in one instance, fractionation occurs at a temperature and pressure that is above the critical point for both carbon dioxide and the alcohol used in fractionation but at a temperature and/or pressure below the critical point for water. Fractionation does not require the presence of three separate phases. In one theory, the conditions produce an aqueous phase and a supercritical phase. One or more products of interest preferentially dissolve in the aqueous phase, and one or more products of interest dissolve preferentially in the supercritical phase. The aqueous phase may be pure water, aqueous alcohol, carbonic acid, or a mixture of aqueous alcohol (such as methanol and/or ethanol) and carbonic acid. The supercritical phase may contain carbon dioxide and alcohol (such as methanol and/or ethanol), or the supercritical phase may contain carbon dioxide, water, and alcohol. Without wishing to be bound by any theories, it is believed that in various instances the aqueous phase dissolves certain water-soluble materials of interest (such as xylose) and helps protect them from further reaction as is promoted by the more chemically aggressive supercritical phase.

Any suitable biomass may be used in the invention, such as a lignocellulosic biomass (e.g. wood, corn stover, wheat straw, bagasse, solid municipal organic waste, corn cobs, or citrus peels and pulp waste and the like), corn, cotton fiber, and the like. The biomass may be treated (e.g. mechanically ground using, for instance, using such size-reduction equipment as a hammer-mill, high-shear mixer such as a plate mill, serrated blade in a slurry tank, and/or an in-line colloidal mixer) in order to obtain biomass particles of the desirable size for a particular set of reaction conditions. For example, the biomass may be treated to obtain a biomass having a particle size of, e.g., no more than about 1 inch hydraulic diameter. In various embodiments, the biomass has a particle size of less than about 20 mm, about 5 mm to about 20 mm, about 7 mm to about 20 mm, about 10 mm hydraulic diameter. During the mechanical treatment, the moisture content of the wet feed may be reduced. The biomass post-mechanical treatment may in various embodiments contain up to about 5 wt %, about 5 wt % to about 12 wt % of water. Alternatively, the biomass may be fed to the reaction process as it is received from its collection points.

Prior to reacting with a reactive fluid such as a water/supercritical $C_1$-$C_5$ alcohol mixture, the biomass may optionally be mixed with a fluid to produce a slurry. The slurry may be comprised of, for example, water and/or one or more $C_1$-$C_5$ alcohols such as ethanol. In some embodiments, the slurry may be comprised of the biomass, water, and the $C_1$-$C_5$ alcohol. In some embodiments, the slurry may be comprised of the biomass, water, and ethanol. In some embodiments, the biomass comprises about 1 to about 35 wt % of the slurry. In some embodiments, the biomass comprises about 1 to about 10 wt % of the slurry. In some embodiments, the biomass comprises about 1 to about 5 wt % of the slurry. In some embodiments, the biomass comprises at least 5 wt % of the slurry. In some embodiments, the biomass comprises about 1 to about 50 wt %, about 5 to about 50 wt %, about 5 to about 40 wt %, about 10 to about 35 wt %, about 15 to about 35 wt % of the slurry.

Single Stage Fractionation of Biomass

In one aspect, a biomass is fractionated to cellulose and xylose, and optionally lignin, in a single stage using a reactive fluid comprising water and a $C_1$-$C_5$ alcohol, and optionally $CO_2$. In one instance, the biomass is reacted with a fluid comprising water and a supercritical $C_1$-$C_5$ alcohol. In some embodiments, the $C_1$-$C_5$ alcohol is selected from ethanol, methanol, butanol, or a combination of one of more of ethanol, methanol, and butanol. In some embodiments, the $C_1$-$C_5$ alcohol is ethanol. In some embodiments, the $C_1$-$C_5$ alcohol is methanol. In some embodiments, the $C_1$-$C_5$ alcohol is butanol. The $C_1$-$C_5$ alcohol may be, for example, about 1 wt % to about 99 wt % of the reactive fluid. In some embodiments, the $C_1$-$C_5$ alcohol is about 5 wt % to about 95 wt %, about 10 wt % to about 90 wt %, about 20 wt % to about 80 wt %, about 30 wt % to about 70 wt % or about 40 wt % to about 60 wt % of the reactive fluid. In some embodiments, the $C_1$-$C_5$ alcohol is at least about 10 wt %, at least about 20 wt %, at least about 30 wt %, at least about 40 wt %, at least about 50 wt %, at least about 60 wt %, at least about 70 wt %, at least about 80 wt %, at least about 90 wt % of the reactive fluid. In some embodiments, the $C_1$-$C_5$ alcohol is about 40 wt % to about 55 wt % of the reactive fluid. In some embodiments, the $C_1$-$C_5$ alcohol is about 30 wt % to about 55 wt % of the reactive fluid. In some embodiments, the water is about 1 wt % to about 99 wt % of the reactive fluid. In some embodiments, the water is 5 wt % to about 95 wt %, about 10 wt % to about 90 wt %, about 20 wt % to about 80 wt %, about 30 wt % to about 70 wt % or about 40 wt % to about 60 wt % of the reactive fluid. In some embodiments, the water is at least about 10 wt %, at least about 20 wt %, at least about 30 wt %, at least about 40 wt %, at least about 50 wt %, at least about 60 wt %, at least about 70 wt %, at least about 80 wt %, at least about 90 wt % of the reactive fluid. In some embodiments, the reactive fluid is essentially free of the $C_1$-$C_5$ alcohol. In some embodiments, the reactive fluid is essentially free of the water.

The reactive fluid comprising water and a $C_1$-$C_5$ alcohol may further comprise $CO_2$. In some embodiments, the reactive fluid does not comprise $CO_2$. In some embodiments, the reactive fluid comprises $CO_2$. When present, the $CO_2$ may be, for example, about 5 wt % to about 40 wt % of the reactive fluid. In some embodiments, the $CO_2$ is about 5 wt % to about 20 wt % of the reactive fluid. In some embodiments, the $CO_2$ is about 5 wt % of the reactive fluid. In some embodiments, the aqueous alcoholic solution is saturated with $CO_2$. Generally, the aqueous alcoholic solution becomes saturated with $CO_2$ at about 5 wt % $CO_2$. In some embodiments, the reactant mixture does not comprise a mineral acid.

In some instances, sufficient water is present in the water/alcohol/carbon dioxide mixture to aid hydrolyzing hemi-cellulose and/or dissolve a water-soluble product of interest such as xylose. Because raw biomass processing often removes water from the biomass, it is often helpful to add water to size-reduced biomass prior to processing the biomass in a supercritical reactor. Alcohol can be added as well to form slurry of size-reduced raw biomass in aqueous alcohol. Alternatively, alcohol or aqueous alcohol can be introduced into the reactor as a separate stream from the biomass, which enters dry, in water, in alcohol, in aqueous alcohol, or entrained in carbon dioxide.

Water can serve any of a number of roles in the reaction. Water can dissolve in carbon dioxide to form carbonic acid that acts on biomass to extract, fractionate, and react biomass such as hemi-cellulose. Water can be present as liquid to dissolve compounds such as xylitol. Water can also aid the alcohol in dissolving lignin and e.g. xylitol.

The biomass and reactive fluid are generally reacted at a temperature of about 243° C. to about 300° C. In some embodiments, the reaction temperature is about 250° C. to about 300° C. In some embodiments, the reaction temperature is about 243° C. to about 270° C. In some embodiments, the reaction temperature is about 280° C. to about 300° C. The biomass and reactive fluid are generally reacted at a pressure of at least about 63.8 bar (63 atm). In some embodiments, the reaction pressure is about 63.8 bar to about 220 bar. In some embodiments, the reaction pressure is about 70 bar to about 130 bar. In some embodiments, the reaction pressure is about 80 bar. In some embodiments, the reaction temperature is about 243° C. to about 300° C., and the reaction pressure is about 63.8 bar to about 220 bar. In some embodiments, the reaction temperature is about 250° C. to about 300° C. and the reaction pressure is about 70 bar to about 130 bar. In some embodiments, the reaction temperature is about 280° C. to about 300° C., and the reaction pressure is about 80 bar. In some embodiments, the water is sub-critical water. In some embodiments, the water is near-critical water. In some embodiments, the $CO_2$ is supercritical $CO_2$. In some embodiments, the $C_1$-$C_5$ alcohol is supercritical and the water is sub-critical. In some embodiments, the $C_1$-$C_5$ alcohol and the $CO_2$ are supercritical, and the water is sub-critical.

The reaction conditions (e.g. reaction temperature and pressure) may be maintained for the length of time needed to produce the desired reaction products. In some embodiments, the biomass is treated for about 0.1 min to about 60 min. In some embodiments, the biomass is treated for about 10 sec to about 60 min. In some embodiments, the biomass is treated for about 0.1 min to about 30 min. In some embodiments, the biomass is treated for about 0.17 min to about 15 min. In some embodiments, the biomass is treated for about 10 sec to about 3 min. In some embodiments, the biomass is treated for about 10 sec to about 1 min. The reaction conditions are selected based on the products to be produced from the biomass, and in many instances, reaction times are on the order of seconds.

Two-Stage Fractionation of Biomass

In another aspect, a biomass is fractionated to cellulose, xylose, optionally lignin and other products, in a two-stage process. The process accomplishes hemicellulose hydrolysis in the first stage with water and $CO_2$; and fractionates, e.g. cleanly fractionates, cellulose and lignin, e.g. high-quality lignin, in the second stage with a $C_1$-$C_5$ alcohol, e.g. ethanol or butanol.

In the first stage, addition of carbon dioxide to the compressed water promotes the formation of carbonic acid, which enhances hydrolysis of hemicellulose at relatively low reaction severity. The advantage with $CO_2$ is the ability to adjust reaction acidity without addition of strong acids or bases. Also, $CO_2$ can be recovered and recycled. The addition of $CO_2$ can significantly enhance polysaccharide hydrolysis rates and hence, increase yields of monomeric sugars, and suppress the formation of HMF byproducts relative to that observed with comparable mineral acid-catalyzed processes.

In the second stage, addition of a $C_1$-$C_5$ alcohol (e.g. ethanol or butanol) dissolves lignin leaving cellulose in solid phase. Cellulose and lignin are separated by filtering the second stage slurry. Solids from filtration contain mostly cellulose. After evaporation of ethanol/butanol from the filtrate, lignin is precipitated.

During the physicochemical treatment stage of the biomass, the molecular structures of the complex polymers that comprise the biomass particles are altered. The hemicellulose fraction of biomass is hydrolyzed to C5 and C6 sugar molecules (primarily xylose, glucose, and arabinose), and the lignin fraction is separated from the lignocellulose complex and becomes dissolved in the aqueous alcoholic solvent. This process does not generally chemically alter the lignin, other than to produce smaller fragments. The resulting lignin is of a lower molecular weight than the native one in biomass, but no chemical alteration of the lignin at the monomeric level has happened. In some embodiments, about 60 wt % to about 70 wt % of the original biomass is recovered as xylose and lignin.

The reaction at the single stage fractionation of biomass or at each stage of the two stage fractionation process may be quenched by addition of cooled solvent, for example, cooled water/$C_1$-$C_5$ alcohol. In some embodiments, the reaction is quenched by addition of water/ethanol at about 130° C. In some embodiments, the reaction is quenched by cooling to about 70° C. to about 80° C. and a pressure of about 5-10 bar. The reaction may also be quenched by rapid expansion of at least part of the reactant mixture to a lower pressure, such as atmospheric pressure, as may occur through a throttling valve. This may be accomplished within or outside the reactor. In some embodiments, the entire reactant mixture is rapidly expanded to atmospheric pressure. In some embodiments, for example in a semi-batch reaction, the biomass may be placed in a packed bed, the reactive fluid such as the water/supercritical $C_1$-$C_5$ alcohol, the water/supercritical $CO_2$ or the $C_1$-$C_5$ alcohol is passed through the packed bed to react the biomass, and the extracted solution (comprising the xylose and lignin) is rapidly expanded to atmospheric pressure e.g. through a nozzle. Expansion of the reaction product mixture to atmospheric pressure may be sufficiently rapid to additionally destroy crystalline structure of the cellulose, resulting in amorphous cellulose. The reaction may also be quenched by cooling the reaction mixture in a heat exchanger. In some instances, the reaction is cooled without diluting the products in the reaction mixture.

After the reaction, the insoluble cellulose, which may generally comprise up to about 35-40 wt % of the initial biomass fraction, may be separated from the solvent and the soluble components by conventional methods such as e.g. filtration, centrifugation, etc. Using the single stage method, the lignin, which may generally comprise up to about 20 wt % of the dry biomass, remains dissolved in the water-alcohol solvent where carbon dioxide has been flashed from the mixture, and the lignin may be separated from the xylose and other sugars and un-reacted hemicellulose, which are also dissolved in the water-alcohol solvent, by conventional methods. For example, by evaporating the $C_1$-$C_5$ alcohol, the lignin will precipitate out of solution, while the xylose remains dissolved in the remaining water. The lignin may then be separated by e.g. filtration, centrifugation, etc. In another example, after filtration of the cellulose, the solvent is evaporated, resulting in a solid comprising lignin and xylose. Addition of water to this solid will dissolve only the xylose, which may be separated from the lignin by e.g. filtration. In some embodiments, up to about 80% of the lignin in the original biomass is recovered. Xylose may be separated from other sugars and hemicellulose by conventional methods known in the art.

In the two stage methods for biomass fractionation, the majority of the hemicellulose in the biomass may be hydrolyzed to form xylose and/or xylose oligosaccharides (referred to as "xylose/XOS" herein) in the first stage. Xylose/XOS is obtained in the liquid phase. The remaining solid from the first stage is processed further to separate lignin from cellulose. The lignin is dissolved in the alcohol and the cellulose remains as a solid.

In some instances, the mixture comprising the biomass and the reactive fluids is preheated before entering the reactor, e.g. in a furnace or a heat exchanger. In some instances, the reactive fluids are preheated before contacting the biomass in a reactor. The pressure required for the fractionation reaction can be applied by suitable means known in the art, such as a high pressure piston pump for delivering fluid to the reactor or a pressure exerted by an inert gas such as nitrogen. The pressure can be maintained by, for example, a back pressure regulator located downstream of the reactor.

The cellulose, lignin and xylose products obtained may be analyzed using known methods. For example, lignin can be analyzed using UV-Vis spectrometry or GC/MS; xylose can be analyzed using HPLC; cellulose can be analyzed using acid hydrolysis followed by HPLC.

Figure 2:
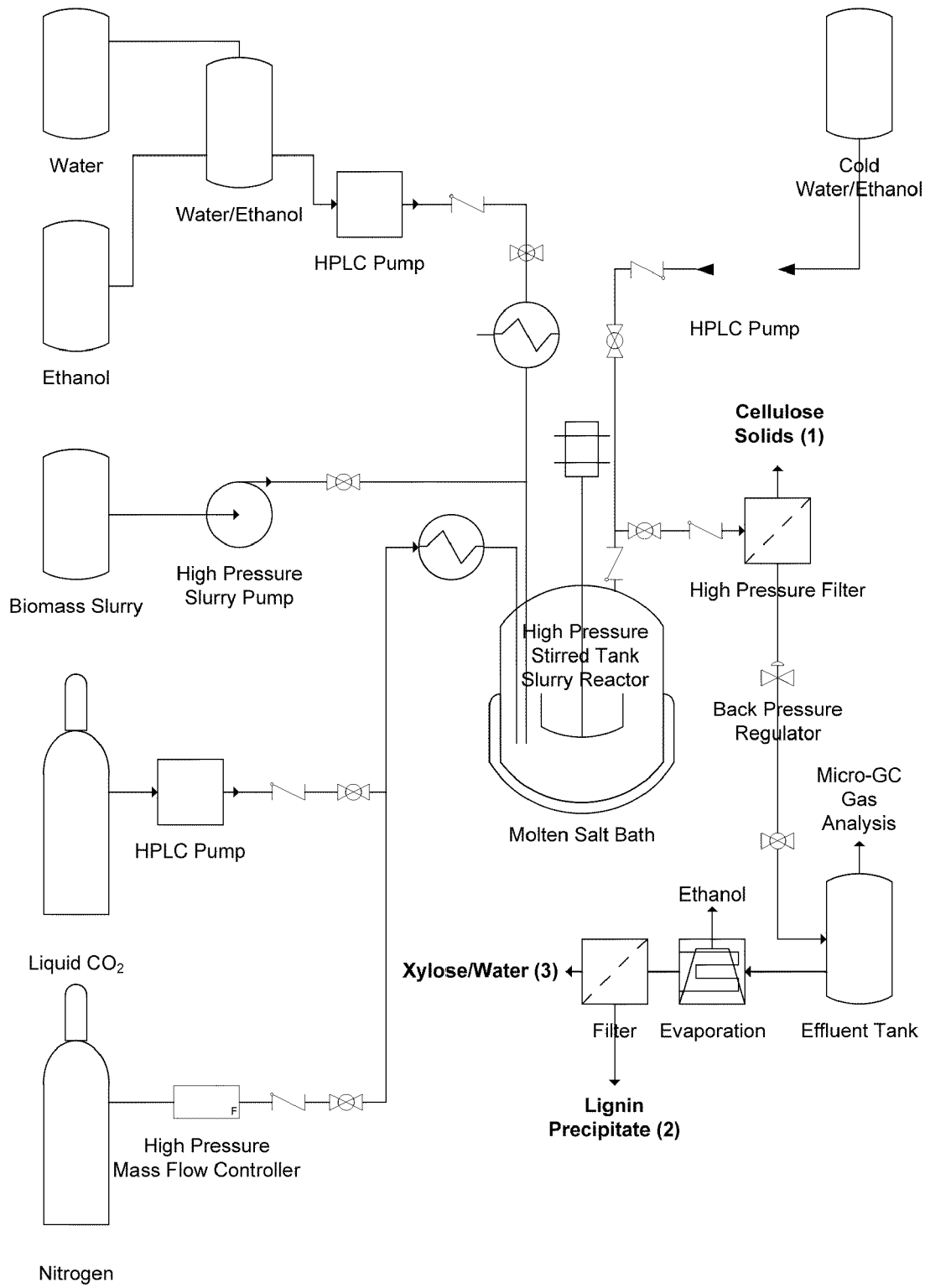
FIG. 2 depicts one embodiment of a reactor system for continuous biomass fractionation.

The methods of the invention can be practiced in a batch process, a semi-batch process or a continuous process, and may utilize conventional chemical reactor technology. One non-limiting example of a continuous process is illustrated in FIG. 2. The reaction schematic in FIG. 2 may also be modified for use in a batch or semi-batch process.

In some embodiments, the process is a semi-batch process for fractionating a biomass comprising: adding the biomass to a reactor bed; passing a fluid comprising water, $C_1$-$C_5$ alcohol, and optionally $CO_2$ through the biomass at a first temperature and a first pressure for a first time period, wherein the $C_1$-$C_5$ alcohol is supercritical at the first temperature and first pressure; quenching the reaction to form one or more reaction product mixtures comprising one or more fractionated products; and recovering one or more fractionated products. In some embodiments, the reaction is quenched by rapidly expanding the extracted fluid (i.e. the fluid which has passed through the packed bed) to atmospheric pressure. In some embodiments, while the fluid is not passing through the biomass packed bed, the bed is purged with a stream of nitrogen gas.

In some embodiments, the process is a batch process for fractionating a biomass comprising: loading the biomass, water, $C_1$-$C_5$ alcohol, and optionally $CO_2$ into a batch reactor to form a reactant mixture; heating the reactant mixture to a first temperature and a first pressure for a first time period, wherein the $C_1$-$C_5$ alcohol is supercritical at the first temperature and first pressure; quenching the reaction to form one or more reaction product mixtures comprising one or more fractionated products; and recovering one or more fractionated products.

In some embodiments, the process is a batch or continuous process for fractionating a biomass comprising: (a) feeding a slurry of the biomass in a first fluid comprising water and a $C_1$-$C_5$ alcohol, a second fluid comprising water and a $C_1$-$C_5$ alcohol, and optionally a third fluid to a reactor, wherein the biomass, first fluid, second fluid, and optional third fluid form a reactant mixture; (b) maintaining the reactant mixture in the reactor at a first temperature and first pressure for a first time period, wherein the $C_1$-$C_5$ alcohol is supercritical at the first temperature and first pressure, and wherein a reaction occurs; (c) quenching the reaction, wherein one or more reaction product mixtures comprising one or more fractionated products are produced; and (d) recovering one or more fractionated products from the one or more reaction product mixtures. The slurry may optionally be pre-heated prior to entering the reactor, for example, so that the reactant mixture is at or near the first temperature and/or first pressure prior to entering the reactor. For example, slurry may be mixed with pre-heated second fluid prior to entering the reactor. The reactor may also be pre-heated to the desired temperature and/or pressure prior to loading the reactor with the slurry. The $CO_2$ may be mixed with the slurry (e.g. before or after pre-heating of the slurry), mixed with the second fluid, and/or added separately to the reactor. The reaction may be quenched inside or outside of the reactor, for example, by expanding the reactant mixture or a portion thereof to a lower pressure (e.g. atmospheric pressure). Alternatively or additionally, the reaction may be quenched by adding a cooled fluid (e.g. cooled water/alcohol) to the reactant mixture. The fractionated products may be collected from the cooled effluent stream from the reactor at several stages. In one embodiment, the effluent mixture (the reaction product mixture) is passed through a high pressure filter. The solids that do not pass the filter may be collected and rinsed with e.g. a water/$C_1$-$C_5$ alcohol mixture (e.g. a water/ethanol mixture), yielding the cellulose product which is insoluble in the mixture. The filtrate that passes through the filter contains soluble products, e.g. lignin and xylose. The filtrate may be collected, e.g. in an effluent tank. When $CO_2$ is fed to the reactor, the bulk of it may be separated from the water/$C_1$-$C_5$ alcohol mixture in the effluent tank. The $C_1$-$C_5$ alcohol may then be evaporated from the mixture, causing lignin to precipitate from the solution. This may then be filtered, and lignin product collected. The xylose/XOS product may be collected from the remaining water solution.

Also provided by the invention is a process for fractionating a biomass comprising the steps of: (a) feeding a slurry of the biomass in a first fluid comprising water and a $C_1$-$C_5$ alcohol, a second fluid comprising water and a $C_1$-$C_5$ alcohol, and optionally a third fluid to a reactor, wherein the biomass, first fluid, second fluid, and optional third fluid form a reactant mixture; (b) maintaining the reactant mixture in the reactor at a first temperature and first pressure for a first time period, wherein the $C_1$-$C_5$ alcohol is supercritical at the first temperature and first pressure, and wherein a reaction occurs; (c) quenching the reaction, wherein one or more reaction product mixtures comprising one or more fractionated products are produced; and (d) recovering one or more fractionated products from the one or more reaction product mixtures.

In some embodiments, the process for fractionating a biomass is a single stage process comprising: (a) feeding a slurry comprising a biomass in a first fluid comprising water and a $C_1$-$C_5$ alcohol and optionally $CO_2$ to a reactor, wherein the biomass, first fluid, and optional $CO_2$ form a reactant mixture; (b) maintaining the reactant mixture in the reactor at a first temperature and first pressure for a first time period, wherein the $C_1$-$C_5$ alcohol is supercritical at the first temperature and first pressure, and wherein a reaction occurs; (c) quenching the reaction, wherein one or more reaction product mixtures comprising one or more fractionated products are produced; and (d) recovering one or more fractionated products from the one or more reaction product mixtures. In some embodiments, the slurry comprising the reactant mixture is heated before fed to the reactor. In some embodiments, the reaction is quenched by cooling the reaction mixture, for example, by passing through a heat exchanger.

Also provided by the invention is a process for fractionating a biomass comprising the steps of: (1) preparing a slurry of the biomass in a water/ethanol mixture; (2) heating the biomass slurry to a first temperature by mixing with a stream of a heated water/ethanol mixture; (3) feeding the heated biomass slurry and optionally $CO_2$ to a reactor maintained at the first temperature and a first pressure to form a reactant mixture; (4) maintaining the reactant mixture in the reactor for a first time period; (5) allowing the reactant mixture to flow out of the reactor (the effluent mixture); (6) cooling the effluent mixture by mixing with a stream of a cold water/ethanol mixture; (7) passing the cooled effluent mixture through a high pressure filter to collect the solids that do not pass the filter; (8) rinsing the solids collected with a water/ethanol mixture to remove soluble components; (9) collecting the insoluble solid as a first solid product; (10) collecting the filtered fluid from step (7) in an effluent tank; (11) evaporating ethanol from the filtered fluid collected in the effluent tank to precipitate a second solid product; (12) collecting the second solid product by filtration; and (13) collecting an aqueous filtrate from step (12). In some embodiments, a $CO_2$ stream is fed to the reactor in step (3). In this case, the filtered fluid from step (7) that is collected in the effluent tank contains $CO_2$, which may optionally either be refluxed under supercritical conditions or liquefied under sub-critical conditions. In some embodiments, $CO_2$ is not added to the reactor.

The following laboratory-scale examples of STP illustrate the invention. A plant size system of this invention operating, e.g. in a continuous mode, can use biomass of larger particle sizes than those described in the examples below e.g. less than about 1 inch hydraulic diameter. Pumps or other mechanisms capable of handling high-solids slurries and industrially relevant ways of heat transfer are embraced by the methods and processes of this invention. Examples of modifications which may be used on an industrial scale include recovering heat through jacketed pipe heat exchangers.

In some embodiments, the process for fractionating a biomass, such as a lignocellulosic biomass, is a two stage process comprising: (a) forming a first reactant mixture comprising a biomass, water and $CO_2$ at a first temperature and a first pressure; (b) maintaining the first reactant mixture at the first temperature and the first pressure for a first time period, wherein a first reaction occurs; (c) recovering a solid from the first reaction mixture; (d) contacting the solid with a second fluid comprising a $C_1$-$C_5$ alcohol to form a second reactant mixture at a second temperature and a second pressure; (e) maintaining the second reactant mixture at the second temperature and the second pressure for a second time period, wherein a second reaction occurs; and (f) quenching the second reaction to form at least one reaction product mixture. In some embodiments, the process is a continuous process. In some embodiments, the process is a batch process or a semi-batch process. In some embodiments, the first reactant mixture is formed by mixing a slurry of a biomass in water with $CO_2$.

Figure 5:
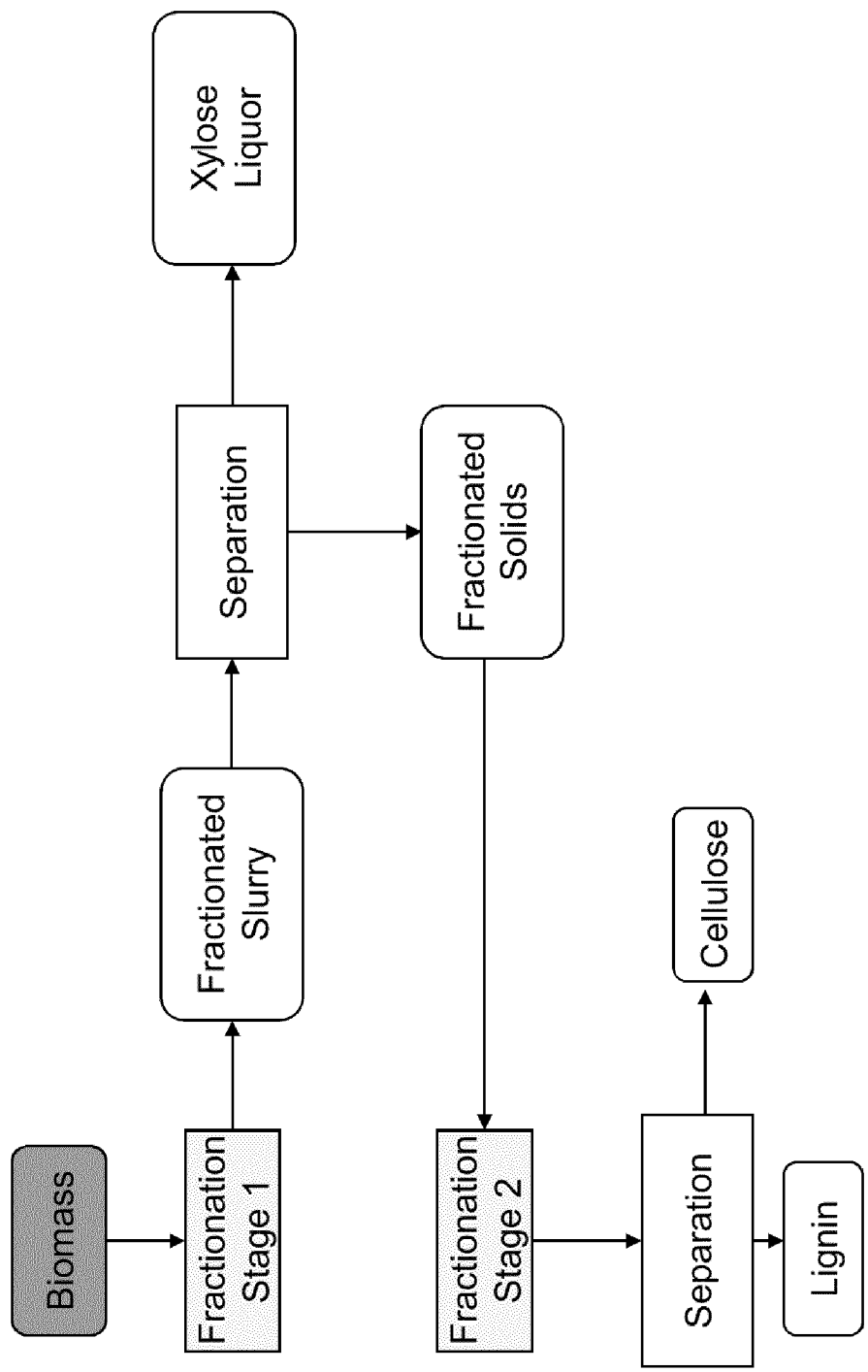
FIG. 5 is a schematic of a two-stage biomass fractionation.

Schematic of the two-stage fractionation process is shown in FIG. 5. A high-pressure reactor system is used for continuous fractionation of biomass in two stages. The reactors operate at temperatures and pressures of up to 350° C. and 100 bar, respectively. The reactor systems are equipped with auxiliary systems, i.e., a high pressure process gas and liquid feeding system; a liquid product collection system; and a data monitoring and acquisition system.

In some embodiments, the first stage in the two stage fractionation of biomass may comprise the following steps: (1) preparing a slurry of the biomass in water; (2) heating the slurry, e.g. in a furnace; (3) mixing $CO_2$ with the slurry to form a reactant mixture; (4) feeding the reactant mixture to the first stage reactor, e.g. continuously by a high-pressure slurry pump, wherein a reaction occurs; (5) quenching the reaction; (6) passing the quenched reaction mixture through a filter to remove insoluble solids and particulate matters; and (7) collecting the filtrate, e.g. in an effluent tank. In some embodiments, liquid $CO_2$ is fed (from another line) directly into the slurry using a special $CO_2$ pump. In some embodiments, the slurry reaches reaction temperature before entering the reactor. The pressure may be maintained by a back pressure regulator located downstream of the reactor. In some embodiments, at the end of reaction time, the effluent exiting the reactor is immediately quenched near the outlet by a heat exchanger. In some embodiments, the cooled reactor effluent is passed through a high-pressure filter to remove solids and particulate matter, and the filtrate is collected in an effluent tank. The xylose-rich solution is analyzed on an HPLC for identification and quantification of sugar products.

In some embodiments, the second stage in the two stage fractionation of biomass may comprise the following steps: (1) mixing the insoluble solids from the first stage with a $C_1$-$C_5$ alcohol (e.g. ethanol or butanol) to form a second reactant mixture; (2) heating the second reactant mixture to a reaction temperature; (3) feeding the heated second reactant mixture to the second stage reactor, e.g. continuously by a high-pressure slurry pump, where a second reaction occurs; (4) quenching the second reaction; (5) passing the quenched reaction mixture through a filter to remove insoluble solids and particulate matters; and (6) collecting the filtrate, e.g. in an effluent tank. The pressure is maintained, e.g. by a back pressure regulator located downstream of the reactor. In some embodiments, at the end of reaction time, the effluent exiting the reactor is immediately quenched near the outlet by heat exchanger. In some embodiments, the cooled reactor effluent is passed through a high pressure filter to remove solids and particulate matter, and the filtrate is collected in an effluent tank. The insoluble solids are analyzed and quantified for cellulose content. Lignin dissolved in the $C_1$-$C_5$ alcohol (e.g. ethanol or butanol) is precipitated by evaporating/distilling ethanol/butanol from the solution.

Also provided is a system for fractionating biomass to form at least one of cellulose and xylose, and optionally lignin, comprises a reactor configured for contacting a biomass with a reactive fluid at a temperature and pressure above the critical point of carbon dioxide but at least one of the temperature and pressure of the fluid is beneath the critical temperature and pressure for water. In some embodiments, the system comprises a reactor configured for contacting a biomass with a reactive fluid at a temperature and pressure at, above or near the critical point water. In some embodiments, the reactor is configured for contacting a biomass with a reactive fluid at a temperature of up to about 250° C., about 300° C., about 350° C., about 375° C. or about 400° C. and a pressure of up to about 100 bar, about 150 bar, about 200 bar, about 250 bar, about 300 bar, or about 350 bar. In some embodiments, the system further comprises a heating device configured for heating the reactive fluid to the desired temperature and a back-pressure regulator located downstream of the reactor for maintaining the desired pressure. In some embodiments, the system may further comprise a heat exchanger configured for cooling a reaction located downstream of the reactor. In some embodiments, the system may further comprise a filtration device configured for separating solids and particulate matters from liquids in a reaction mixture, such as a high-pressure filter. In some embodiments, the system may further comprise a second reactor configured for contacting a biomass with a reactive fluid at a temperature and pressure above the critical point of carbon dioxide but at least one of the temperature and pressure of the fluid is beneath the critical temperature and pressure for water.

In a particular embodiment, the system for fractionating biomass to form at least one of cellulose and xylose, and optionally lignin, comprising: a heater for heating the reactant mixture; a reactor for fractionating the biomass, mechanically coupled to the heater for receiving the heated reactant mixture; and a heat exchanger mechanically coupled with the reactor for receiving and cooling the fractionated reactant mixture. In some embodiments, the system further comprises a filtration device for separating at least a portion of the fractionated product in solid state from the fractioned and cooled reactant mixture. The reactor in the system of the invention is any reactor capable of sustaining the severe temperatures and pressures under which the fractionation reaction occurs, such as a tube constructed to sustain the temperature and pressure suitable for fractionating biomass. The heater of the system can be any suitable heater. Non-limiting examples of the heater include furnace, oven, heating blanket and heat exchanger (e.g. a tube heat exchanger or a shell heat exchanger. The heat exchanger for cooling the reaction mixture after may be a tube heat exchanger or a shell heat exchanger.

In some embodiments, any of the system may further comprise additional apparatus such as vessels for holding the fluids or slurry, devices for monitoring the temperatures and pressures, and modules for date collection and safety controls.

In some embodiments, the system for fractionating biomass to form at least one of cellulose and xylose, and optionally lignin; further comprises a reactant mixture including a biomass, water, a $C_1$-$C_5$ alcohol, and optionally $CO_2$.

In some embodiments, provided is a composition comprising a biomass, water and a $C_1$-$C_5$ alcohol. In some embodiments, the $C_1$-$C_5$ alcohol is a supercritical $C_1$-$C_5$ alcohol. Water and supercritical $C_1$-$C_5$ alcohol together form the reactive fluid for fractionating biomass. In some embodiments, the $C_1$-$C_5$ alcohol is selected from ethanol, methanol, butanol, or a combination of one of more of ethanol, methanol, and butanol. In some embodiments, the $C_1$-$C_5$ alcohol is ethanol. In some embodiments, the $C_1$-$C_5$ alcohol is methanol. In some embodiments, the $C_1$-$C_5$ alcohol is butanol. The $C_1$-$C_5$ alcohol may be, for example, about 1 wt % to about 99 wt % of the reactive fluid. In some embodiments, the $C_1$-$C_5$ alcohol is about 5 wt % to about 95 wt %, about 10 wt % to about 90 wt %, about 20 wt % to about 80 wt %, about 30 wt % to about 70 wt % or about 40 wt % to about 60 wt % of the reactive fluid. In some embodiments, the $C_1$-$C_5$ alcohol is at least about 10 wt %, at least about 20 wt %, at least about 30 wt %, at least about 40 wt %, at least about 50 wt %, at least about 60 wt %, at least about 70 wt %, at least about 80 wt %, at least about 90 wt % of the reactive fluid. In some embodiments, the $C_1$-$C_5$ alcohol is about 40 wt % to about 55 wt % of the reactive fluid. In some embodiments, the $C_1$-$C_5$ alcohol is about 30 wt % to about 55 wt % of the reactive fluid. In some embodiments, the water is about 1 wt % to about 99 wt % of the reactive fluid. In some embodiments, the water is 5 wt % to about 95 wt %, about 10 wt % to about 90 wt %, about 20 wt % to about 80 wt %, about 30 wt % to about 70 wt % or about 40 wt % to about 60 wt % of the reactive fluid. In some embodiments, the water is at least about 10 wt %, at least about 20 wt %, at least about 30 wt %, at least about 40 wt %, at least about 50 wt %, at least about 60 wt %, at least about 70 wt %, at least about 80 wt %, at least about 90 wt % of the reactive fluid. In some embodiments, the reactive fluid is essentially free of the $C_1$-$C_5$ alcohol. In some embodiments, the reactive fluid is essentially free of the water.

In some embodiments, provided is a composition comprising a biomass, water, a $C_1$-$C_5$ alcohol and optionally $CO_2$. In some embodiments, the $C_1$-$C_5$ alcohol and the optional $CO_2$ in the reactant mixture both are in supercritical state. In such instances, water, supercritical $C_1$-$C_5$ alcohol and the optional supercritical $CO_2$ together form the reactive fluid. In some embodiments, the reactive fluid does not comprise $CO_2$. In some embodiments, the reactive fluid comprises $CO_2$. When present, the $CO_2$ may be, for example, about 5 wt % to about 40 wt % of the reactive fluid. In some embodiments, the $CO_2$ is about 5 wt % to about 20 wt % of the reactive fluid. In some embodiments, the $CO_2$ is about 5 wt % of the reactive fluid. In some embodiments, the aqueous alcoholic solution is saturated with $CO_2$. Generally, the aqueous alcoholic solution becomes saturated with $CO_2$ at about 5 wt % $CO_2$. In some embodiments, the reactant mixture does not comprise a mineral acid.

Fractionation of biomass such as a lignocellulosic biomass produces cellulose, xylose/XOS and lignin. Therefore, the invention provides compositions comprising a product produced by any of the processes described herein, such as a cellulose product, a xylose product (e.g. xylose/XOS), a lignin product, or a mixture thereof.

The invention can be further understood by reference to the following examples, which are provided by way of illustration and are not meant to be limiting.

EXAMPLES

Example 1

A Semi-Batch Process for Biomass Fractionation

Corn stover was obtained from the National Renewable Energy Laboratory (NREL). The corn stover was processed using a grinder to produce 40 mesh corn stover. The 40 mesh particle size was found to be suitable for use in the laboratory-scale supercritical fluid extraction process.

Treatment of corn stover with supercritical ethanol-$CO_2$ mixtures was carried out using a semi-batch reactor (see FIG. 1). The corn stover was held in the bed 6 by a 20 micron sintered metal frit placed at the downstream end of the bed. During sand bath 4 heating up, the system was purged with nitrogen. Once at the desired temperature, ethanol/$CO_2$ flow from the reservoir 2 was started using the HPLC pump 3, passing first through a preheating coil 5, and then through the corn stover. Solvent temperature was monitored at the bed entrance by a thermocouple. After passing through the corn stover, the solvent was expanded through a nozzle 7 to atmospheric pressure, which quenched the reaction.

For each run, corn stover was loaded into the packed bed reactor 6. The reactor assembly was placed in the sand bath 4. The sand bath 4 was heated to 264° C., during which time the reactor 6 was purged with flowing nitrogen. Heating up time was in the range of 200-230 minutes. Once at 264° C., the transfer line heat tracing was brought to 250° C. The nitrogen flow was stopped and the HPLC pump was started. The system was brought to a pressure of 1100 psig (except where noted below) and the pump flow rate was adjusted to give a constant system pressure. Extraction of the corn stover was carried out for a period of 20 minutes, after which the pump was stopped and the system was allowed to depressurize. Once the system pressure dropped to below 300 psig, the nitrogen flow was restarted and the system was cooled to room temperature. Preparation and testing of several nozzles led to selection of one which provided a suitable pressure drop at the desired flow rates. The expansion nozzle 7 was fabricated from a Swagelok tubing which was modified by pinching to produce a suitable pressure restriction.

Following the extraction, any solids remaining in the packed bed were recovered and massed. The product solutions recovered during extraction were evaporated to dryness at ~50° C. in room air. The solid residue was washed with 20 mL of warm water. This water soluble portion was added to a sample container and evaporated to dryness at 110° C. The water insoluble portion, comprising lignin, was re-dissolved in ethanol, added to a sample container, and evaporated to dryness at 110° C. These two solid fractions comprise the water soluble and ethanol soluble fractions, respectively.

Run 1—Supercritical Ethanol and Supercritical $CO_2$

The ethanol was held under 300 psig $CO_2$ pressure overnight before the reaction. Using a flow rate of 5.4 mL liquid/min a constant system pressure of 1200 psig was achieved. Product was observed almost immediately as an amber colored solution in the condenser. Extraction continued for 20 minutes. The solid recovered from the packed bed (primarily cellulose) was darker than the starting material, but appeared to have the same particle size and was free flowing. Results are given in Table 1.

TABLE 1

Experimental results showing corn stover load and various solids recovered

| Run | 1 |
|---|---|
| Solvent | scEtOH/scCO$_2$ |
| Corn Stover Loaded (g) | 0.3064 |
| Recovered solids left over in bed (g) | 0.1919 |
| Extract (wt %) (EtOH and water soluble solid fractions) | 37.4 |
| Ethanol Soluble (g) | * |
| Water Soluble (g) | * |

*Amounts not measured. The calculated sum of ethanol soluble and water soluble fractions is up to 0.1145 g.

Supercritical ethanol/$CO_2$ removed a significant amount of material from corn stover. About 37.4% of the initial mass of corn stover appeared in the ethanol-soluble and water-soluble fractions of the extract. The ethanol soluble fraction component was confirmed to be lignin using GC-MS.

Example 2

A Batch Process for Biomass Fractionation

One set of experiments were done using a 1.2 ml batch reactor made of Swagelok stainless steel tube and Techne SB-2 fluidized sand bath. Corn stover (40 mesh size) was used for this set of experiments.

Calculated amounts of 40 mesh size corn stover (1 g dry basis VF), 3 g liquid (50/50 wt % mixture of water and ethanol) and 5-20 wt % dry ice (based on liquid weight) were taken into the Swagelok stainless steel tube. This tube was heated in a sand bath with varying temperature (180° C. to 320° C.) and pressure (75-80 bar) for various time intervals (0.17 min to 15 min). After the heat treatment, the reaction was quenched by immersing the tube into a water bath maintained at 25° C. The reaction product mixture obtained from this treatment was filtered to obtain a solid product comprising cellulose. The filtrate was evaporated in an oven maintained at 75° C. The residual solid obtained was added to water at 60° C., and the resulting solution filtered. This filtrate was analyzed by HPLC for xylose content, and the solid was analyzed by GC-MS for lignin content.

As shown in Table 2, the mass of corn stover solubilized (xylose and lignin) (as a % of theoretical) using different experimental conditions was tabulated against time, temperature, a constant liquid/solid (L/S) ratio (the EtOH/water/$CO_2$ liquid to corn stover solid), and the lignin fraction recovered.

TABLE 2

Experimental results showing mass solubilized and lignin fraction recovered at various temperatures and residence times

| S. No. | Temperature (° C.) | Residence Time (min) | L*/S ratio | Mass Solubilized as % theoretical | Lignin fraction recovered as % incoming biomass |
|---|---|---|---|---|---|
| 1 | 270 | 2 | 3 | 51.2 | 19.7 |
| 2 | 270 | 3 | 3 | 57.6 | 16.3 |
| 3 | 280 | 2 | 3 | 58.1 | 19 |
| 4 | 280 | 3 | 3 | 66.8 | 18.7 |
| 5 | 285 | 2 | 3 | 67.1 | 18.7 |
| 6 | 285 | 3 | 3 | 69.3 | 17.6 |
| 7 | 300 | 0.17 | 3 | 45.8 | 17.1 |
| 8 | 300 | 0.17 | 3 | 54.5 | 21.1 |
| 9 | 300 | 0.50 | 3 | 49.6 | 17.8 |
| 10 | 300 | 0.50 | 3 | 53.9 | 20.1 |
| 11 | 300 | 0.50 | 3 | 59.1 | 20.7 |
| 12 | 300 | 1 | 3 | 62.2 | 23.1 |
| 13 | 300 | 1 | 3 | 61.7 | 20.3 |

*Liquid was 5 wt % dry ice in a 50/50 mixture of water and ethanol

It was observed that around 270° C., the slope of mass solubilized vs. T increased. This may be due to undesirable cellulose degradation and loss from parasitic reactions. At 285° C. and 2-3 min, about 67-70% of mass was solubilized. Concentrations of $CO_2$ greater than that necessary to maintain saturation in the liquid phase (about 5%) had little effect on yields (data not shown). Temperatures above 300° C. at longer residence times yielded increasing decomposition of cellulose (data not shown).

The data in the following table were generated using similar methodology and corn stover as substrate. As expected, lower temperatures result in lower mass solubilized. Since cellulose content in corn stover is about 33%, about 67% mass solubilized is desired in this step. It is preferable to operate at a temperature of about 250° C. or more so that the length of time needed to extract products of interest from biomass is commercially feasible, and lower liquid to solid (L/S) ratios can be used.

TABLE 3

| Temperature, ° C. | Residence time, min | L/S ratio | $CO_2$ conc., wt % | Ethanol conc., wt % | Mass solubilized, % |
|---|---|---|---|---|---|
| 180 | 15 | 1 | 5 | 40 | 20.3 |
| 240 | 15 | 6 | 5 | 40 | 52.1 |
| 270 | 3 | 3 | 33 | 33 | 57.6 |
| 280 | 3 | 3 | 33 | 33 | 66.8 |
| 285 | 2 | 3 | 33 | 33 | 67.1 |
| 300 | 1 | 3 | 33 | 33 | 62.5 |
| 300 | 1.5 | 3 | 33 | 33 | 68.8 |
| 320 | 0.17 | 3 | 33 | 33 | 69.9 |
| 320 | 0.5 | 3 | 33 | 33 | 74.9 |

Example 3

Continuous Fractionation of Biomass-I

A high pressure, continuously stirred slurry reactor system is used for continuous fractionation of biomass (see FIG. 2).

The slurry reactor is of relatively large volume (100 ml) and operates at temperatures and pressures up to 350° C. and 1,100 psig. The reactor system is equipped with auxiliary systems including a high pressure process gas and liquid feeding system; a liquid product collection system; and a data monitoring and acquisition system. Samples of liquid and gas products are acquired continuously. Similar stirred reactors have been successfully used by other researchers to study hydrothermal processing of biomass (Osada M, Sato T, Watanabe M, Adschiri T, Arai K. "Low-Temperature Catalytic Gasification of Lignin and Cellulose with a Ruthenium Catalyst in Supercritical Water" *Energy Fuels* 2004, 18:327-333).

In this steady-state experimental setup, biomass is first mechanically treated to obtain a particle size of less than about 500 μm. Following this, biomass slurry (1-5 wt %) is prepared in an aqueous solution containing ethanol. Next, this slurry is fed to the reactor continuously by a high pressure slurry pump, and mixed with preheated water/ethanol solution that is fed by an HPLC pump before entering the reactor. This premix ensures that slurry reaches reaction temperature before entering the reactor. The slurry reactor is heated by a molten salt bath. Pressure is maintained by a back pressure regulator located downstream of the reactor. From another line, liquid $CO_2$ is fed directly to the reactor using an HPLC pump. Next, at the end of the reaction time, the effluent exiting the reactor is immediately quenched near the outlet by mixing with cold water/ethanol fed by another HPLC pump. This cooling reactor effluent is passed through a high pressure filter to remove solids, and the filtrate is collected in an effluent tank after passing through the back pressure regulator. Gas is sampled from the headspace and sent to GC for analysis. Ethanol is evaporated to precipitate lignin, which is isolated by filtration, and the remaining water comprising xylose is analyzed on an HPLC for identification and quantification of sugar products. The insoluble solid is analyzed and quantified for cellulose fiber content. Lignin is analyzed with GC-MS.

The experiments are done to develop kinetic data that are not available in the open literature. In non-isothermal Thermogravimetric Analysis (TGA) studies of biomass pyrolysis, which has some relationship to solvothermal processing, Rao and Sharma (Rao T R & Sharma A "Pyrolysis rates of biomass materials" *Energy* 1998, 23:973-978) showed that the reaction order with respect to the residual biomass fraction can vary from zero to two depending upon the temperature range of the reaction, which suggests that the reaction mechanism changes with temperature or with the procession of the process. The first experiments are aimed to establish the reaction order(s) and activation energies for the major solvothermal processes (hemicellulose hydrolysis and lignin depolymerization) as a function of temperature ranges for baseline liquid phase composition.

Because of the small particle size of biomass material (<500 μm), heat and mass transfer resistances are expected to be negligible, and the reactor is assumed to operate in the kinetic regime. This will allow development of kinetic data that can be used to design larger systems.

Example 4

A Flow-Through Process for Biomass Fractionation

Figure 3:
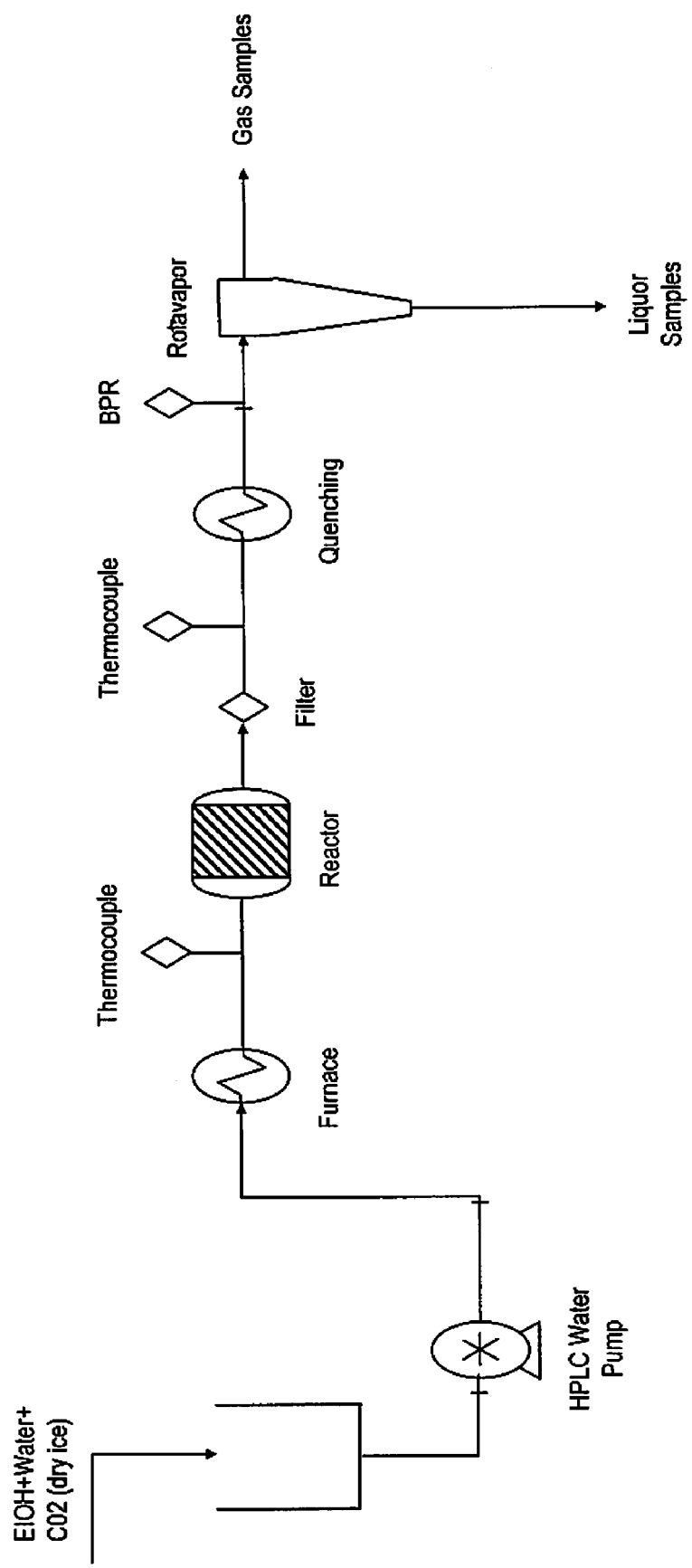
FIG. 3 depicts a schematic of the experimental setup for one embodiment of a single stage flow-through system using 50/50 wt % mixture of ethanol-water as solvent.

A single stage flow-through process is carried out using a high pressure tube reactor made of Swagelok stainless steel tube (see FIG. 3). The reactor volume is 13 ml and biomass used for this set of experiments is birch. Other equipments used for this experiment include $\frac{1}{8}^{th}$ inch Swagelok stainless steel tube; HPLC water pump from Waters-510, furnace; 15 microns Swagelok filter; dry ice as a CO2 supplier; band heater from Cole-Palmer and a Rotavapor.

Calculated amounts of ethanol/water mixture with 3 g liquid (50/50 wt % mixture of water and ethanol) and 5-20 wt % dry ice (based on liquid weight) were allowed to pass through the water pump and then taken into the $\frac{1}{8}^{th}$ inch Swagelok stainless steel tube. The mixture flows at a flow rate of 5 ml/min through the tube and this tube was heated in a furnace with temperature rising from 25° C. to 200° C. and pressure is maintained at 1400-1500 psig. After the heat treatment through the furnace, this mixture is fed to the 13 ml reactor where calculated amount of birch (2 g dry basis) is present and is maintained at a particular temperature with the help of Cole-Palmer band heater. With this set up, the reaction time in the reactor is maintained at 2 min by taking biomass porosity of 0.4 into consideration for calculating this reaction time. For this set of experiments the samples were collected for reactor temperatures of 240° C., 250° C. and 260° C. These temperature and pressures are chosen for this experiment to allow the reaction to occur at supercritical conditions. The 13 ml reactor is followed by 15 micron size filter to restrict the flow of solids along with the liquor. After filtration, the obtained liquor is quenched to temperature 25-30° C. by immersing the tube in the water bath. The filtrate (liquid samples) are collected, evaporated in an oven at 75° C. and analyzed by HPLC for xylose and lignin content. This filtrate is also allowed to be analyzed in GC-MS for any furfural content. The sample collector is connected to a Rotavapor where any escaping gas is condensed by cooling water and is collected in the sampler. The residual solids is removed from the reactor was dried, added to water at 60° C. and the resulting solution is filtered and this filtrate is also analyzed by HPLC for cellulose content, lignin content and evaluate glucan purity of the remaining solids.

The data in the following table were generated for the single stage flow through experiments with similar methods and birch as a substrate. We can observe that as we increase the temperature, the lignin fraction recovered shows an increasing trend from 17-25% as ethanol acts as an extracting solvent. This also shows some interesting results in xylose and furfural contents ranging from 59-66%. Having done the entire solid and liquor analysis it is observed that 250° C. and 2 min reaction time gives better results in terms of solubility, glucan purity and xylose/furfural recovery.

TABLE 4

| Sample No. | 1 | 2 | 3 |
|---|---|---|---|
| Temperature (° C.) | 240 | 250 | 260 |
| Solubility (%) | 38.3 | 70.3 | 33.4 |
| Solids left (%) | 61.7 | 29.7 | 66.6 |
| Glucan purity (%) | 57.4 | 61.2 | 70.6 |
| Glucose recovery (%) | 56.9 | 47 | 61.1 |
| Xylose (%) | 55 | 56 | 61.2 |
| Xylose + Furfural (%) | 59 | 63.5 | 65.7 |
| Lignin fraction recovered as % incoming biomass | 17.5 | 21.2 | 24.5 |

Example 5

Continuous Fractionation of Biomass-II

Figure 4:
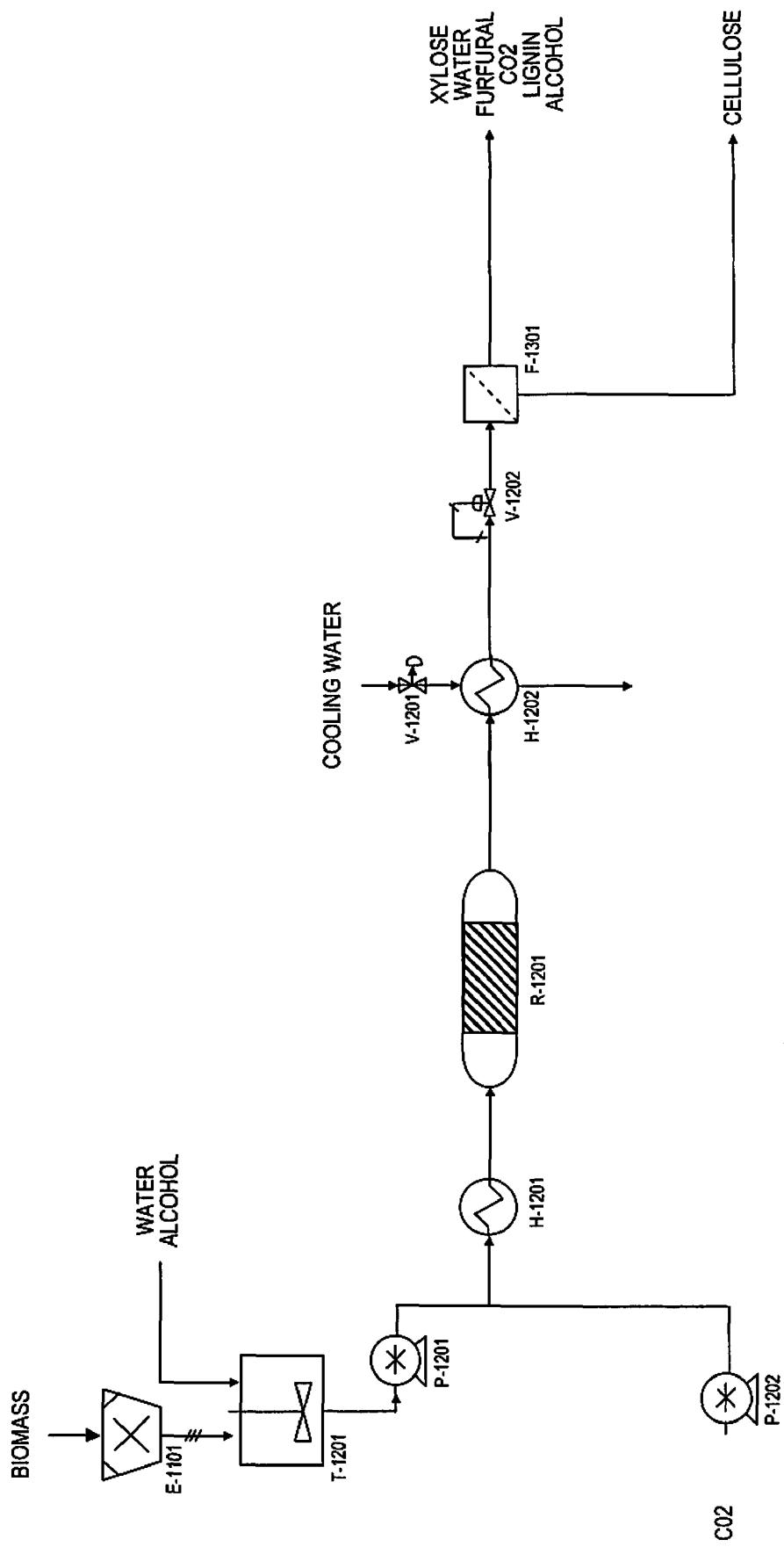
FIG. 4 depicts one embodiment of a reactor system for continuous biomass fractionation.

A high pressure, tube reactor system is used for continuous fractionation of biomass (see FIG. 4). The slurry reactor is of relatively large volume (700 ml) and operates at temperatures and pressures up to 300° C. and 1,500 psig. The reactor system is equipped with auxiliary systems including a high pressure process gas and liquid feeding system; and a solid and liquid product collection system. Samples of liquid and gas products are acquired continuously.

In this steady-state experimental setup, biomass is first mechanically treated to obtain a particle size of less than about 500 µm. Following this, biomass slurry (5-10 wt %) is prepared in an aqueous solution containing ethanol. Next, this slurry is fed to the heater continuously by a high pressure slurry pump From another line, liquid $CO_2$ is fed directly and mixed with the slurry stream using an high pressure pump. The slurry stream passes through a tube furnace which heats the slurry stream to reaction temperature before entering the reactor. The slurry reactor is heated by band heaters. Pressure is maintained by a back pressure regulator located downstream of the reactor. Next, at the end of the reaction time, the effluent exiting the reactor is immediately quenched by a cooling water heat exchanger. The cooled stream then passes though the back pressure regulator, after which the pressure reduces to ambient pressure. This reactor effluent is passed through a filter to remove and collect solids, and the filtrate is collected in an effluent tank. Gas is sampled from the headspace and sent to GC for analysis. Ethanol is evaporated to precipitate lignin, which is isolated by filtration, and the remaining water comprising xylose is analyzed on an HPLC for identification and quantification of sugar products. The insoluble solid is analyzed and quantified for cellulose fiber content. Lignin is analyzed with GC-MS.

The experiments are done to develop kinetic data that are not available in the open literature. In non-isothermal Thermogravimetric Analysis (TGA) studies of biomass pyrolysis, which has some relationship to solvothermal processing, Rao and Sharma (Rao T R & Sharma A "Pyrolysis rates of biomass materials" *Energy* 1998, 23:973-978) showed that the reaction order with respect to the residual biomass fraction can vary from zero to two depending upon the temperature range of the reaction, which suggests that the reaction mechanism changes with temperature or with the procession of the process. The first experiments are aimed to establish the reaction order(s) and activation energies for the major solvothermal processes (hemicellulose hydrolysis and lignin depolymerization) as a function of temperature ranges for baseline liquid phase composition.

Because of the small particle size of biomass material (<500 µm), heat and mass transfer resistances are expected to be negligible, and the reactor is assumed to operate in the kinetic regime. This will allow development of kinetic data that can be used to design larger systems.

Example 6

Continuous Fractionation of Biomass in Two Stages (a) General Process

Schematic of the two-stage fractionation process is shown in FIG. 5. A high-pressure reactor system is used for continuous fractionation of biomass in two stages. The reactors operate at temperatures and pressures of up to 350° C. and 100 bar, respectively. The reactor systems are equipped with auxiliary systems, i.e., a high pressure process gas and liquid feeding system; a liquid product collection system; and a data monitoring and acquisition system.

In this experimental setup, biomass slurry is prepared in water. Next, this slurry is heated in a furnace and fed to the first stage reactor continuously by a high-pressure slurry pump. From another line, liquid $CO_2$ is fed directly into the slurry using a special $CO_2$ pump. The slurry reaches reaction temperature before entering the reactor. Pressure is maintained by a back pressure regulator located downstream of the reactor. At the end of reaction time, the effluent exiting the reactor is immediately quenched near the outlet by a heat exchanger. This cooled reactor effluent is passed through a high-pressure filter to remove solids and particulate matter, and the filtrate is collected in an effluent tank. This xylose-rich solution is analyzed on an HPLC for identification and quantification of sugar products.

The insoluble solids from the first stage are mixed with $C_1$-$C_5$ alcohol (e.g. ethanol or butanol) and then fed to the second stage reactor continuously by a high-pressure slurry pump and heated to reaction temperature before entering the reactor in a manner similar to that in the first stage. Pressure is maintained by a back pressure regulator located downstream of the reactor. At the end of reaction time, the effluent exiting the reactor is immediately quenched near the outlet by heat exchanger. This cooled reactor effluent is passed through a high pressure filter to remove solids and particulate matter, and the filtrate is collected in an effluent tank. The insoluble solids are analyzed and quantified for cellulose content. Lignin dissolved in the $C_1$-$C_5$ alcohol (e.g. ethanol or butanol) is precipitated by evaporating/distilling ethanol/butanol from the solution.

(b) Materials

The biomass feedstock used was hardwood flour (mix of oak and birch) from American Fiber, which contains ~36% glucan, ~17% xylan and ~32% lignin.

The two-stage fractionation was conducted in a pilot plant capable of processing 100 kg/d of dry biomass. An 8-10% hardwood flour slurry in water was processed in the first stage. The resultant solids from the first stage were fed to the second stage as 8-10% slurry in butanol.

(c) Process Conditions

Stage 1: 250° C., 100 bar, 1 min residence time, 1:1 $CO_2$/biomass; Stage 2: 250° C., 100 bar, 1 min residence time, butanol as solvent.

(d) Results

In stage 1, about 71.1% of xylan accounted for, including 57.3% as xylose oligomers, 7.0% as xylose monomers, and 6.8% as furfural. In stage 2, 88.9% of remaining xylan was dissolved, while about 0.1% of glucan was dissolved. Glucan content in the resultant solids was about 74-78%. A >90% overall delignification was achieved.

Although the foregoing invention has been described in some detail by way of illustration and example for purposes of clarity of understanding, it will be apparent to those skilled in the art that certain changes and modifications may be practiced without departing from the invention. Therefore, the descriptions and examples should not be construed as limiting the scope of the invention.

It should be noted that, as used herein, the singular form "a", "an", and "the" includes plural references unless indicated otherwise. Additionally, as used herein, the term "comprising" and its cognates are used in their inclusive sense; that is, equivalent to the term "including" and its corresponding cognates.

All patents, patent applications, documents, and articles cited herein are incorporated by reference in their entireties.

What is claimed is:

1. A process comprising:
   (a) contacting a biomass and a reactive fluid comprising water and supercritical $C_1$-$C_5$ alcohol to form a reactant mixture at a first temperature and a first pressure; wherein the $C_1$-$C_5$ alcohol is present at a level of about 40 wt % to about 55 wt % in said reactive fluid;

wherein the first temperature is about 243° C. to about 300° C.;

(b) maintaining the reactant mixture at the first temperature and first pressure for a first time period, wherein a reaction occurs; and (c) optionally quenching the reaction to form at least one reaction product mixture; wherein a product selected from the group consisting of xylose and cellulose is produced by the process.

2. The process of claim 1, wherein lignin is produced by the process.

3. The process of claim 1 or 2, further comprising:
(d) recovering one or more products selected from the group consisting of cellulose, xylose and lignin from the at least one reaction product mixture.

4. The process of claim 2, further comprising:
(d) filtering the at least one reaction product mixture to produce a first solid and a first reaction product mixture filtrate, wherein the first solid comprises cellulose, and the first reaction product mixture filtrate comprises xylose and lignin.

5. The process of claim 4, further comprising:
(e) partitioning the first reaction product mixture filtrate into a water soluble fraction and an ethanol soluble fraction, wherein the water soluble fraction comprising xylose and the ethanol soluble fraction comprises lignin.

6. The process of claim 1 or 2, wherein the biomass is a lignocellulosic biomass.

7. The process of claim 1, wherein the water is sub-critical water.

8. The process of claim 1, wherein the water is near-critical water.

9. The process of claim 1, wherein the $C_1$-$C_5$ alcohol is selected from the group consisting of methanol, ethanol, and butanol.

10. The process of claim 1, wherein the reactive fluid further comprises supercritical $CO_2$.

11. The process of claim 10, wherein the reactive fluid is about 5 wt % to about 20 wt % $CO_2$.

12. The process of claim 1, wherein the first pressure is about 63.8 bar to about 220 bar.

13. The process of claim 1, wherein the first time period is about 0.1 min to about 60 min.

14. The process of claim 1, wherein prior to contacting with the reactive fluid, the biomass is present as a slurry.

15. The process of claim 1, wherein the process is a batch process, a semi-batch process or a continuous process.

16. A process for fractionating a biomass comprising:
(a) feeding a slurry comprising a biomass in a first fluid comprising water and a $C_1$-$C_5$ alcohol and optionally $CO_2$ to a reactor, wherein the biomass, first fluid, and optional $CO_2$ form a reactant mixture;
wherein the $C_1$-$C_5$ alcohol is present at a level of about 40 wt % to about 55 wt % in said first fluid;
(b) maintaining the reactant mixture in the reactor at a first temperature and first pressure for a first time period, wherein the $C_1$-$C_5$ alcohol is supercritical at the first temperature and first pressure, and wherein a reaction occurs;
wherein the first temperature is about 243° C. to about 300° C.;
(c) quenching the reaction, wherein one or more reaction product mixtures comprising one or more fractionated products are produced; and
(d) recovering one or more fractionated products from the one or more reaction product mixtures.

17. A process for fractionating a biomass comprising:
(a) forming a first reactant mixture comprising a biomass, water, and $CO_2$ at a first temperature and a first pressure;
(b) maintaining the first reactant mixture at the first temperature and the first pressure for a first time period, wherein the $CO_2$ is supercritical and the water is sub-critical, and wherein a first reaction occurs;
wherein the first temperature is about 243° C. to about 300° C.;
(c) recovering a solid from the first reaction mixture;
(d) contacting the solid with a second fluid comprising a $C_1$-$C_5$ alcohol to form a second reactant mixture at a second temperature and a second pressure;
(e) maintaining the second reactant mixture at the second temperature and the second pressure for a second time period, wherein a second reaction occurs; and
(f) quenching the second reaction to form at least one reaction product mixture.

* * * * *